United States Patent [19]

Bock et al.

[11] Patent Number: 5,517,022
[45] Date of Patent: May 14, 1996

[54] APPARATUS FOR MEASURING AN AMBIENT ISOTROPIC PARAMETER APPLIED TO A HIGHLY BIREFRINGENT SENSING FIBER USING INTERFERENCE PATTERN DETECTION

[75] Inventors: Wojtek J. Bock, Gloucester, Canada; Waclaw Urbanczyk, Wroclaw, Poland

[73] Assignee: Universite Du Quebec A Hull, Hull, Canada

[21] Appl. No.: 237,189

[22] Filed: May 3, 1994

[51] Int. Cl.⁶ .................................................... G01J 1/04
[52] U.S. Cl. ................... 250/227.17; 250/231.19; 250/225; 356/351; 356/1
[58] Field of Search .................. 250/231.19, 227.14, 250/227.16, 227.17, 225; 73/705, 715; 356/35.5, 351

[56] References Cited

U.S. PATENT DOCUMENTS

| | | | |
|---|---|---|---|
| 3,625,616 | 12/1971 | Lee | 356/107 |
| 4,275,963 | 6/1981 | Primbsch | 356/35.5 |
| 4,421,384 | 12/1983 | McMahon | 350/96.29 |
| 4,428,239 | 1/1984 | Johnston | 73/705 |
| 4,495,411 | 1/1985 | Rashleigh | 250/227 |
| 4,725,143 | 2/1988 | Jones | 356/351 |
| 4,740,081 | 4/1988 | Martens et al. | 356/345 |
| 4,758,087 | 7/1988 | Hicks, Jr. | 356/345 |
| 4,882,716 | 11/1989 | Lefevre et al. | 367/149 |
| 4,904,863 | 2/1990 | McDearmon | 260/227 |
| 4,920,261 | 4/1990 | Bock et al. | 250/225 |
| 5,032,026 | 7/1991 | Jouve et al. | 356/351 |
| 5,054,922 | 10/1991 | Kersey | 356/345 |
| 5,064,270 | 11/1991 | Turpin et al. | 350/96.29 |
| 5,087,124 | 2/1992 | Smith et al. | 356/358 |
| 5,138,155 | 8/1992 | Gray | 250/231.19 |
| 5,179,424 | 1/1993 | Lequime et al. | 356/351 |
| 5,187,983 | 2/1993 | Bock et al. | 73/705 |
| 5,200,796 | 4/1993 | Lequime | 356/346 |
| 5,317,147 | 5/1994 | Dandliker et al. | 250/227.17 |

*Primary Examiner*—Edward P. Westin
*Assistant Examiner*—Steven L. Nichols
*Attorney, Agent, or Firm*—Collard & Roe

[57] ABSTRACT

An apparatus and a method are provided for measuring an ambient physical parameter applied to a highly birefringent sensing fiber. A light source emits a low coherence light beam into a sensing fiber subjected to an ambient physical parameter. A collector receives the output light beam of the sensing fiber and a splitter divides the output light beam into two orthogonally polarized output beams and subjects the two orthogonally polarized output beams to a range of relative delays. A recombiner combines the two orthogonally polarized output beams to produce an interference pattern, and a detector detects intensities of the interference pattern over the range of delays. A calculating device determines the ambient parameter from the intensities with improved accuracy.

13 Claims, 5 Drawing Sheets

APPARATUS FOR MEASURING AN AMBIENT ISOTROPIC PARAMETER APPLIED TO A HIGHLY BIREFRINGENT SENSING FIBER USING INTERFERENCE PATTERN DETECTION

BACKGROUND OF THE INVENTION a) Field of the Invention

The present invention relates to an apparatus and a method for measuring an ambient physical parameter, and for example high hydrostatic pressure, applied to a highly birefringent sensing optical fiber.

b) Description of the Prior Art

Ambient physical parameters such as temperature, pressure and magnetic fields affect the propagation properties of optical fibers. Birefringent sensing fibers are a special type of optical fibers. They are characterized by two orthogonal polarization states allowing simultaneous propagation of two orthogonal polarization modes. Upon application of an ambient physical parameter, the two orthogonal polarization modes propagate at different velocities, thus creating a relative delay between the two orthogonal polarization modes, proportional to a value of the ambient physical parameter. For example, to measure pressure, U.S. Pat. No. 4,920,261 (Bock et al.) describes the use of a birefringent fiber placed in a pressure chamber, connected to a light source and a measuring apparatus. To measure the relative delay between the two orthogonal polarization modes introduced by pressure, the measuring apparatus detects light signals in a predetermined direction of polarization, locks-in the detected light signals, measures the amplitude of the light signals according to time, and uses a computer to determine the relative delay between the two orthogonal polarization modes using the amplitude of the light signals according to time. This apparatus requires many calculations to determine the ambient pressure. Moreover, this apparatus implies a trade-off between sensitivity and range of measurements since the length of the sensing fiber determines the range of the measurements while the precision of the measurements is indirectly proportional to the range of measurements.

SUMMARY OF THE INVENTION

An object of the present invention is to provide an apparatus which allows large range of measurements without compromising the quality of the results. Another object of the present invention is to provide a method that simplifies the measurement of the relative delay between the two orthogonal polarization modes.

According to the invention, these objects are achieved with an apparatus and a method for measuring an ambient physical parameter applied to a highly birefringent sensing fiber. The apparatus comprises:

a light source for emitting a low coherence light beam into the sensing fiber where the light beam is divided substantially equally into two polarization modes of the sensing fiber and where the two polarization modes are subjected to a relative delay;

a collector for receiving an output light beam of the sensing fiber containing the two polarization modes;

a splitter for dividing the output light beam into two orthogonally polarized output beams and subjecting the orthogonally polarized output beams to a range of relative delays which is larger than and includes the relative delay introduced by the sensing fiber;

a recombiner for combining the divided orthogonally polarized output beams to produce an interference pattern;

a detector for detecting intensities of the interference pattern over the range; and a calculating means for determining the ambient parameter from the intensities. Usually, the calculating means determine the parameter by a position of the peak of the intensities.

Preferably, the collector expands the output light beam and the splitter is a Wollaston prism that splits the output beam into slightly different directions thereon and introduces relative delays increasing linearly from a beginning to an end of the Wollaston prism in a direction of splitting.

Also according to the present invention, this object is achieved with a method for measuring high hydrostatic pressure applied to a highly birefringent sensing fiber. The method comprises the steps of:

emitting a light beam with low coherence;

directing the light beam into the sensing fiber whereby the light beam is divided substantially equally into two polarization modes of the sensing fiber having orthogonal polarization states, these polarization modes being subjected to a relative delay;

collecting an output light beam containing the modes at an end of the sensing fiber;

dividing the output beam containing the polarization modes into two orthogonally polarized output beams and subjecting the orthogonally polarized output beams to a range of relative delays larger than the relative delay introduced by the sensing fiber;

recombining the orthogonally polarized output beams to produce an interference pattern;

detecting intensities across the interference pattern and determining position of the interference pattern; and determining the ambient parameter from position of the interference pattern.

Preferably, the range of relative delays is achieved by passing the orthogonally polarized output beams through a Wollaston prism splitting the beams into slightly different directions thereon and introducing relative delays increasing linearly from a beginning to an end of the Wollaston prism in a direction of splitting.

The low coherence source is preferred because the coherence length of the source is a limiting factor of the range of pressures measured with a single sensing optical fiber.

The step of dividing the output beam and subjecting it to a range of relative delays can be achieved by using an expanded light beam on a wide delay element prism or by using a non-divergent beam on a translating delay element prism and a stationary detector.

BRIEF DESCRIPTION OF THE DRAWINGS

In order to impart a better understanding of the manner in which this object and others are attained in accordance with the present invention, preferred embodiments thereof will be described hereinafter with reference to the accompanying drawings wherein.

In the following description and in the drawings, the same numerals will refer to the same elements.

DESCRIPTION OF PREFERRED EMBODIMENT

Figure 1:
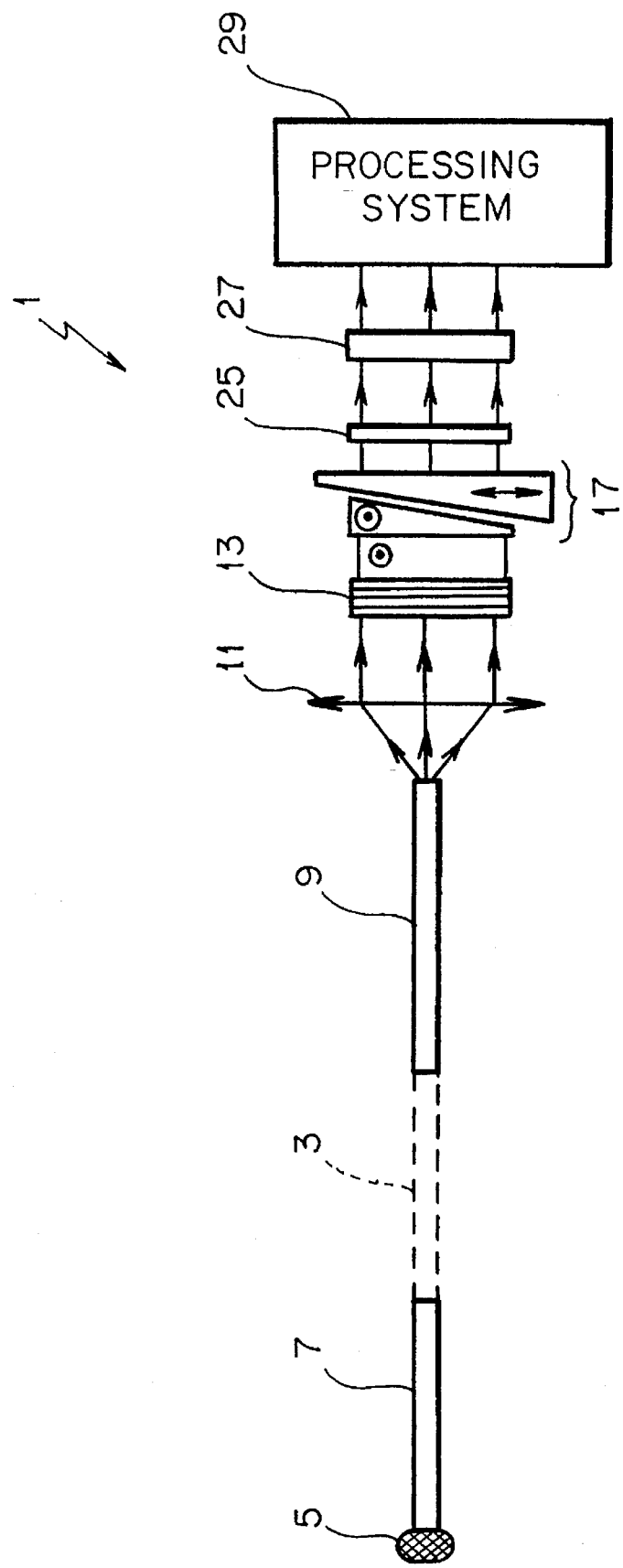
FIG. 1 is a block diagram of an apparatus for measuring an ambient physical parameter applied to a highly birefringent sensing fiber according to the present invention.

Referring to FIG. 1, there is shown an apparatus 1 for measuring an ambient physical parameter applied to a highly birefringent sensing fiber 3 shown in dotted lines. The ambient physical parameter may be for example temperature, pressure, magnetic field or any ambient parameter which affects the quality of birefringence of the fiber, but in the preferred embodiment is high hydrostatic pressure.

The apparatus 1 comprises a light source 5 emitting a low coherence light beam. The light source 5 may consist of a laser diode or a superluminescent diode having a low coherence, such as for example 10–50 microns and a central wavelength $\lambda$. The light source 5 is pigtailed with a lead-in fiber 7 into which the light beam is launched. The lead-in fiber 7 is of a highly birefringent type. This type of fiber propagates only two orthogonally polarized modes having different velocities when excited by a light beam having a wavelength below its cut-off frequency. Thus, the lead-in fiber 7 used in the apparatus 1 has a cut-off wavelength below $\lambda$ to propagate two polarization modes. To get better results, the lead-in fiber 7 is pigtailed to the light source 5 in such a manner that one of its polarization states is aligned to an azimuth of polarization of the light beam, thereby directing all the light beam into the aligned polarization state.

The other end of the lead-in fiber 7 is spliced to the sensing fiber 3 with its polarization modes rotated at 45° with respect to those of the sensing fiber 3. Such a splicing allows an equal division of the light beam into two polarization states of the sensing fiber 3. The pressure applied to the sensing fiber 3 affects its birefringence and propagates two polarization modes having different propagation velocities, and creates a relative delay between them.

The other end of the sensing fiber 3 is spliced to a lead-out fiber 9 of the highly birefringent type, having a cut-off wavelength below $\lambda$. The lead-out fiber 9 has two polarization states rotated of 45° with respect to the polarization states of the sensing fiber 3. To avoid interference between the two polarization modes into the lead-out fiber 9, the relative delay between the two polarization modes introduced by the sensing fiber 9 has to be much greater than the coherence length of the light beam.

A collector 11 is connected to a free end of the lead-out fiber 9. The collector 11 is aligned at 45° with respect to the polarization modes of the lead-out fiber 9 to divide equally the two polarization modes into the two polarization modes of the lead-out fiber, thus improving the results. The collector 11 receives an output light beam of the lead-out fiber 9. The collector 11 is a collimator that receives the output light beam and that transforms that light beam into a parallel light beam. Positive lens of any type, such as a collimating lens, can be used as collector 11, but whatever is the collimator used, it is important to locate the output of the lead-out fiber 9 at a focus of the collimator. Furthermore, to obtain a uniform power distribution of the parallel light beam, the aperture of the collimator has to be less than that of the lead-out fiber 9.

Figure 3:
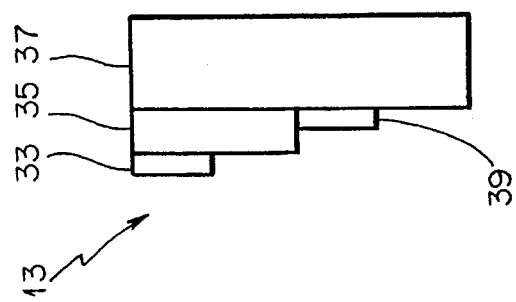
FIG. 3 is a side elevation view of the step delay element of the apparatus shown in FIG. 1.

The parallel light beam passes through a delay element 13 that compensates the relative delay between the two polarization modes introduced by the sensing fiber 3. The delay element 13 is made of a plate of birefringent crystal like quartz or calcite, and its composition and thickness depend on the amount of relative delay to be compensated. To cover a wide range of relative delays, a step delay line 15, as shown on FIG. 3, may be used. The step delay line 15 consists of a superposition of plates 33, 35, 37 and 39 creating several different delays.

A splitter 17 receives the compensated light beam and divides the light beam into two orthogonally polarized output beams, while subjecting the orthogonally polarized output beams to a range of relative delays larger than the delay introduced by the sensing fiber 3. The splitter 17 consists of a Wollaston prism 19 made of birefringent crystal such as calcite or quartz.

Figure 2:
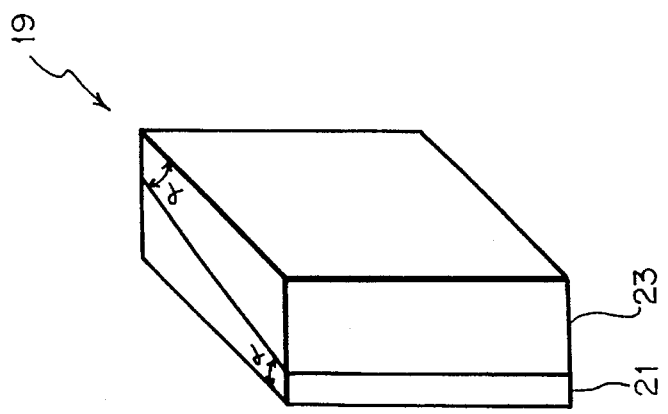
FIG. 2 is a perspective view of the Wollaston prism of the apparatus shown in FIG. 1.

As shown on FIG. 2, the Wollaston prism 19 is composed of two prisms 21 and 23 of identical dimensions, having two optical axes and a wedge $\alpha$. The optical axes of each prism are perpendicular to each other and are parallel to the edges of the two prisms. The polarization axes of the Wollaston prism 19 are aligned with the polarization axes of the step delay line 15, therefore extending the range of relative delays between the two orthogonally polarized output beams.

The Wollaston prism 19 splits the light beam into two slightly different directions, and introduces a range of relative delays increasing linearly from a beginning to an end of the Wollaston prism 19 in a direction of splitting. The angle formed by the different directions is small, per example 2°, and equals the wedge $\alpha$. The range of relative delays introduced by the combination of the Wollaston prism with the step delay element 13 can be much larger than the range of delays introduced by the Wollaston prism 19 alone. The plates 33, 35, 37 and 39 introduce delays, i.e. relative delays between the two modes, which are slightly less than the delay differential from one side to the other of prism 19. Each consecutive plate adds such a delay step, i.e. plate 35 increases the delay by almost a full range with respect to plate 33.

A recombiner 25 is used to combine the split light beam out of the Wollaston prism 19 to produce an interference pattern. The recombiner 25 consists of an analyzer aligned at 45° with the polarization axes of the Wollaston prism.

Figure 4:
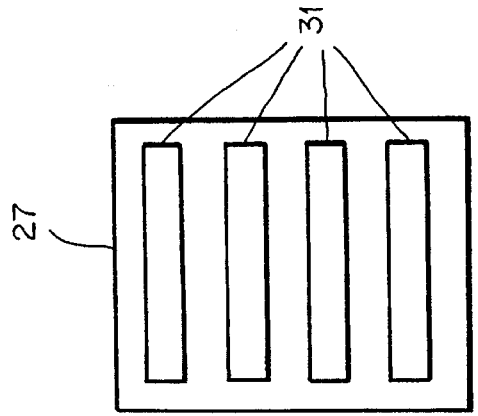
FIG. 4 is a front elevation view of the detector of the apparatus shown in FIG. 1.
Figure 5:
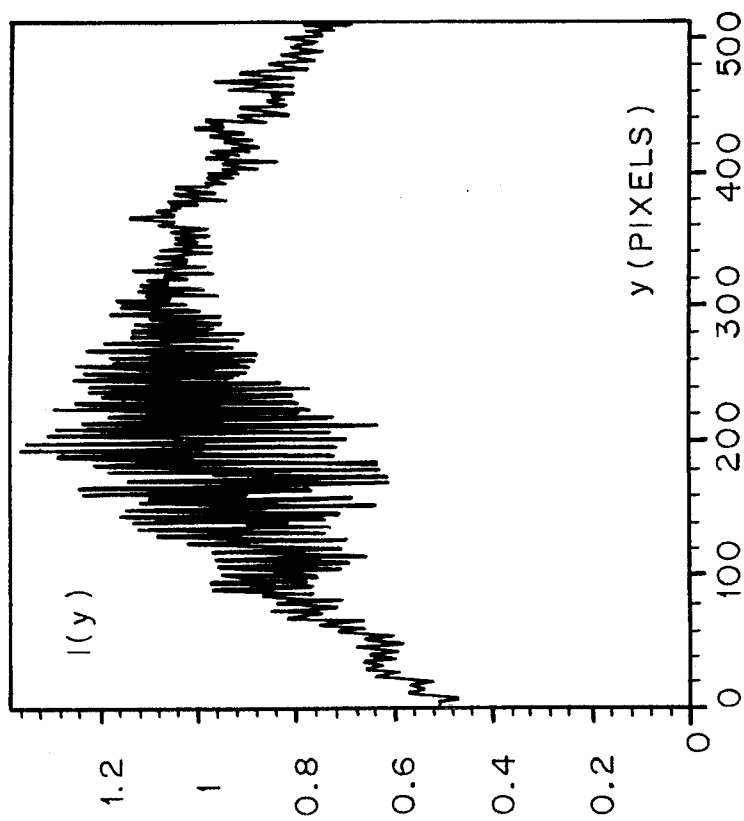
FIG. 5 is a graph showing an example of the intensities detected across the interference pattern with the apparatus of FIG. 1.

The combined light beam is received by a detector 27 that detects the intensities of the light beam across the interference pattern. The detector 27 consists of a Charged Coupled Device with photo-arrays 31. When a step delay line is used, multiple photo-arrays 31 overlapping at their extremities are conventionally used, as shown in FIG. 4. FIG. 5 shows an example of intensities measured across the interference pattern in function of the position where they were measured.

Figure 6:
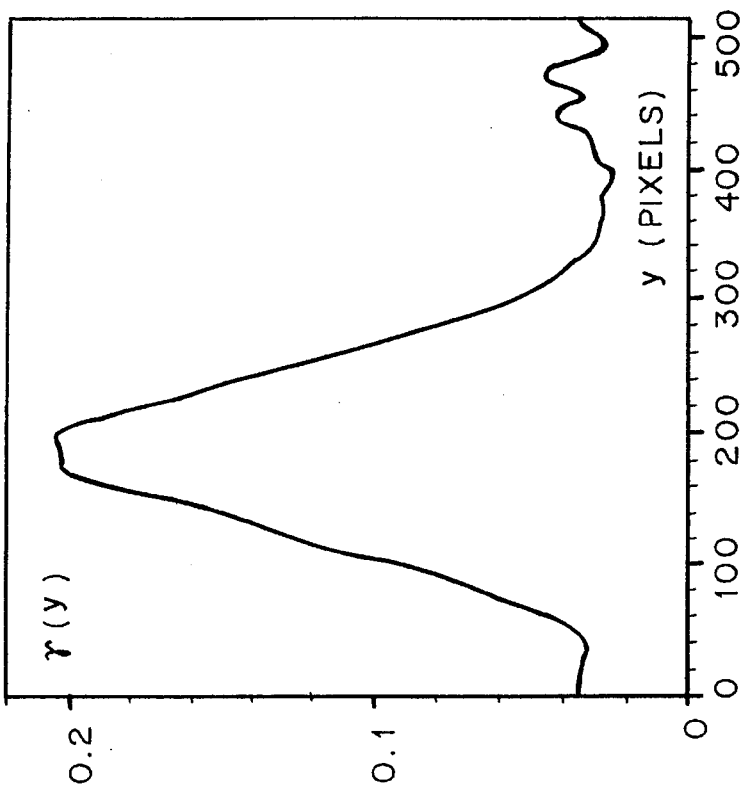
FIG. 6 is a graph showing an example of the position of the interference pattern determined by the apparatus of FIG. 1.

The detector 27 also determines the position of the interference pattern. FIG. 6 shows an example of the position of the interference pattern as a function of the position where they were measured. The mathematical function used to determine the position of the interference pattern from the measured intensities is the following:

$$\gamma(y) = \frac{1}{2\Delta Y_\lambda} \int_{-\Delta Y_\lambda}^{\Delta Y_\lambda} |I_N(y)| dy,$$

where:

y is a pixel across the interference pattern on the CCD, $2\Delta Y_\lambda$ is the width of two interference fringes, $I_N$ corresponds to $I(y)/I_0(y)$, $I(y)$ being the intensities detected across the interference pattern and $I_0(Y)$ being numerical filtering out of higher harmonics from $I(y)$, and $\gamma$ is the position of the interference pattern.

Figure 7:
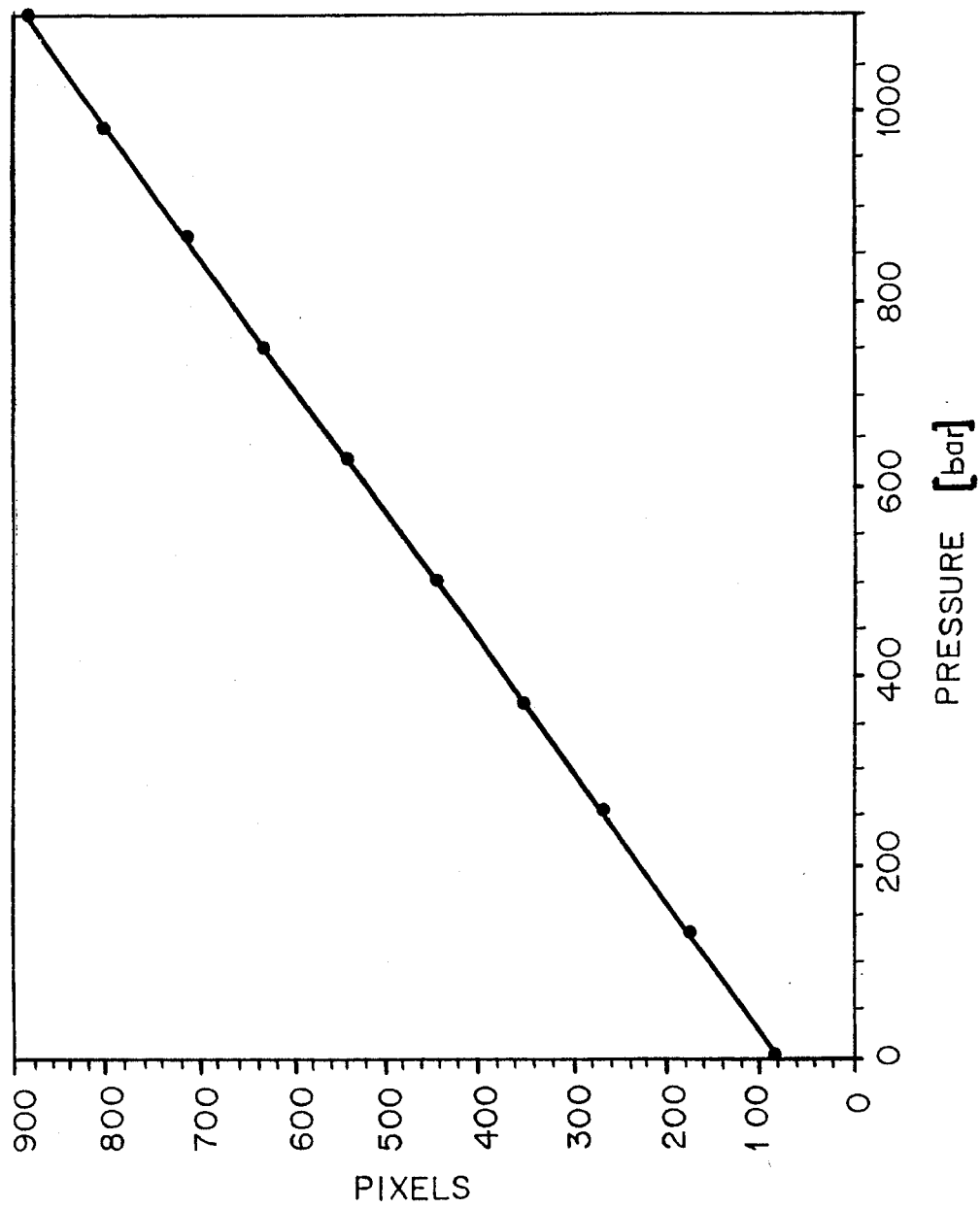
FIG. 7 is a graph showing an example of high hydrostatic pressures corresponding to positions of interference pattern, determined by the apparatus of FIG. 1.

The position of the interference pattern measured by the detector is used by a calculating means 29 to determine the ambient parameter from that position. FIG. 7 shows an example of a graph indicating ambient pressure corresponding to positions of the interference pattern, determined by experimentation. The calculating means 29 may be, for example, a computer having a software tracking the position of the center of the interference pattern.

Figure 8:
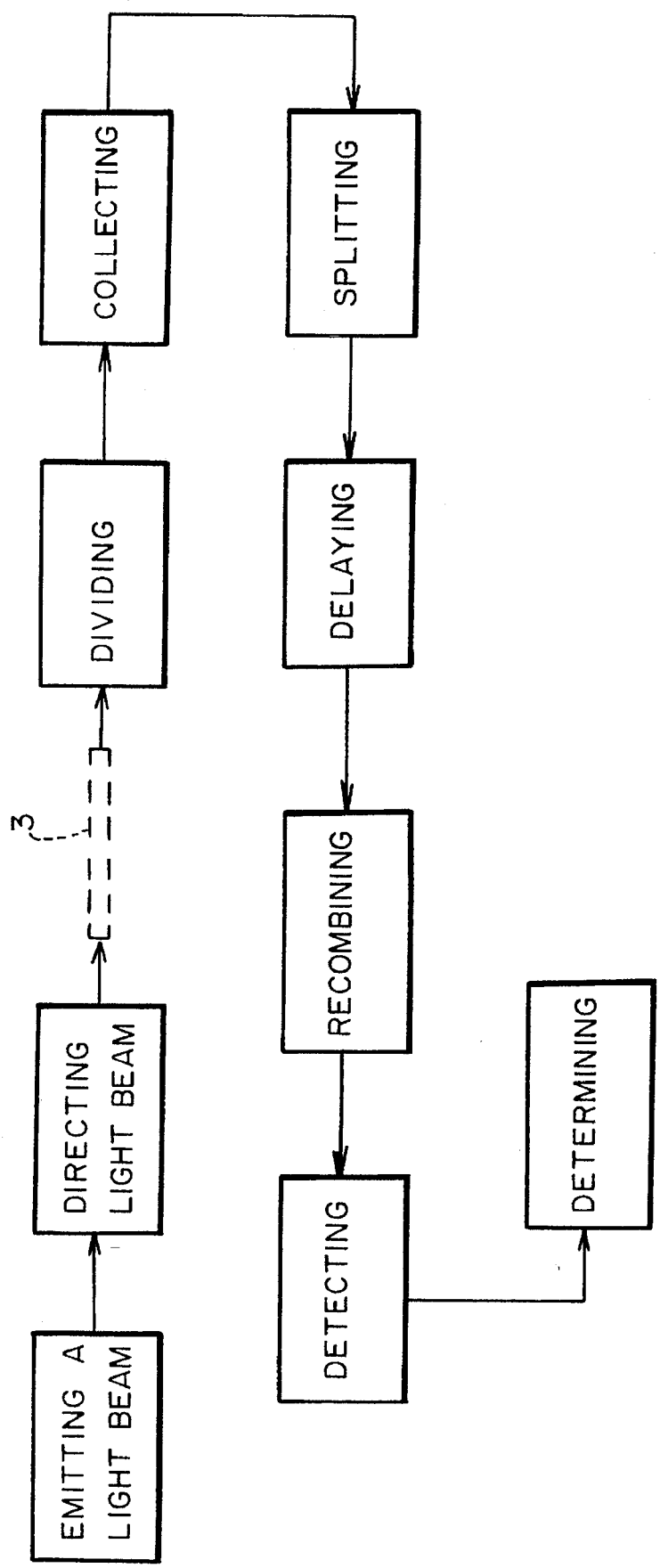
FIG. 8 is a block diagram of a method for measuring an ambient physical parameter applied to a highly birefringent sensing fiber according to the present invention.

Referring to FIG. 8, there is shown a method for measuring an ambient physical parameter applied to a highly birefringent sensing fiber. The method first comprises the steps of emitting a light beam with low coherence, for example 10–50 microns, and having a central wavelength λ below a cut-off wavelength of the sensing fiber. The light beam is directed into the sensing fiber in such a manner that it is divided substantially equally into two polarization modes corresponding to two polarization states of the sensing fiber. The two polarization states of the sensing fiber subject different velocities to the two orthogonally polarization modes, thus creating a relative delay between the two polarization modes.

Then, an output light beam of the sensing fiber containing the two polarization modes is collected at an end of the sensing fiber. The output light beam is split into two orthogonally polarized output beams having slightly different directions. The split orthogonally polarized output beams are subjected to a range of relative delays larger than the relative delay introduced by the sensing fiber.

After their subjection to the range of relative delays, the two orthogonally polarized output beams are recombined to produce an interference pattern. Intensities across the interference pattern are detected and a position of the interference pattern is determined. Finally, from the position of the interference pattern, the ambient parameter is determined.

As can be appreciated, the length of the sensing optical fiber determines the range of the physical parameter (eg. range of pressure) which will cause the phase shift between modes to reach 180°. For the apparatus to operate without initial calibration before each use, its range of operation should correspond to less than a 180° relative phase shift. If such a phase shift corresponds to a pressure range of 0 to 100 atm, it becomes very difficult to obtain accurate measurements, i.e. having an error <±0.1 atm. The analysis of a range of delayed interfering modes provides an improved, more accurate measurement. The step delay line subdivides the range into overlapping groups and further enhances accuracy with a broad range.

I claim:

1. A fiber-optic apparatus for measuring an isotropic ambient physical parameter, said apparatus comprising:

a light source for emitting a low coherence, linearly polarized light beam in a predetermined polarization plane;

a highly birefringent lead-in fiber having an input connected to said light source, a polarization axis parallel to said polarization plane, for propagating a polarization mode excited by said lightbeam, and an output;

a highly birefringent sensing fiber having an input connected to said output of the lead-in fiber, two polarization axes rotated by an angle of 45° with respect to said polarization axis of the lead-in fiber to divide substantially equally said polarization mode propagating in the lead-in fiber into two polarization modes propagating with different velocities in said sensing fiber, and an output where a total relative delay between said two polarization modes in the sensing fiber is a sum of an initial delay caused by a natural birefringence of said sensing fiber and an additional delay induced by the isotropic ambient physical parameter when said sensing fiber is subjected thereto;

a highly birefringent lead-out fiber having an input connected to said output of the sensing fiber, two polarization axes rotated by an angle of 45° with respect to said polarization axes of the sensing fiber for dividing substantially equally said two polarization modes propagating in the sensing fiber into two other polarization modes propagating in said lead-out fiber and subjecting said two other polarization modes to a relative delay substantially different from said total relative delay produced by said sensing fiber, and an output;

a collector for receiving an output light beam comprising said two other polarization modes from said output of the lead-out fiber;

a splitter for dividing said two other polarization modes into two linearly, orthogonally polarized output beams and subjecting said orthogonally polarized output beams to a range of relative delays covering said total relative delay produced by said sensing fiber;

a recombiner for combining said orthogonally polarized output beams to produce an interference pattern;

a detector for detecting intensities across said interference pattern and determining a position of a center of said interference pattern; and a calculating means for determining said ambient parameter from the position of said center of said interference pattern.

2. An apparatus according to claim 1, wherein said splitter comprises:

a crystalline delay plate having polarization axes aligned at an angle of 45° with respect to said polarization axes of the lead-out fiber, for splitting said two other polarization modes in the lead-out fiber into said two linearly, orthogonally polarized output beams and introducing a relative retardation between said output beams, the relative retardation being equal to the initial delay caused by said natural birefringence of the sensing fiber;

at least one step delay crystalline plate combined with said crystalline delay plate, said at least one step delay crystalline plate having polarization axes aligned in parallel to said polarization axes of the crystalline delay plate to extend said range of relative delays; and a Wollaston prism having polarization axes aligned in parallel with said polarization axes of said crystalline delay plate, for diverging said output light beams into slightly different directions thereon and introducing another range of relative delays increasing linearly from a beginning to an end of said Wollaston prism in a direction of diverging.

3. An apparatus according to claim 2, wherein a range of delays introduced by said prism and said step delay crystalline plate is slightly larger than said additional delay induced in said sensing fiber by the isotropic ambient physical parameter.

4. An apparatus according to claim 2, wherein a range of delays introduced by said prism and said step delay crystalline plate is almost twice as large as said other range of delays introduced by said prism alone.

5. An apparatus according to claim 2, wherein said collector is a collimator for collimating said output light beam.

6. An apparatus according to claim 1, wherein said detector is a charged coupled device camera and said calculating means is a computer having a software for tracking the position of said center of the interference pattern.

7. An apparatus according to claim 1, wherein said light source has a coherence length of 10 to 50 microns.

8. A fiber-optic apparatus for measuring an ambient physical parameter, said apparatus comprising:

a light source for emitting a linearly polarized light beam having a coherence length of 10–50 microns, in a predetermined polarization plane;

a highly birefringent lead-in fiber having an input connected to said light source, a polarization axis parallel to said polarization plane, for propagating a polarization mode excited by said lightbeam, and an output;

a highly birefringent sensing fiber having an input connected to said output of the lead-in fiber, two polarization axes rotated by an angle of 45° with respect to said polarization axis of the lead-in fiber to divide substantially equally said polarization mode propagating in the lead-in fiber into two polarization modes propagating with different velocities in said sensing fiber, and an output where a total relative delay between said two polarization modes in the sensing fiber is a sum of an initial delay caused by a natural birefringence of said sensing fiber and an additional delay induced by the isotropic ambient physical parameter when said sensing fiber is subjected thereto;

a highly birefringent lead-out fiber having an input connected to said output of the sensing fiber, two polarization axes rotated by an angle of 45° with respect to said polarization axes of the sensing fiber for dividing substantially equally said two polarization modes propagating in the sensing fiber into two other polarization modes propagating in said lead-out fiber, and for subjecting said two other polarization modes to a relative delay substantially different from said total relative delay produced by said sensing fiber, and an output;

a collimator for receiving an output light beam comprising said two other polarization modes from said output of said lead-out fiber;

a crystalline delay plate having polarization axes aligned at an angle of 45° with respect to said polarization axes of the lead-out fiber, for splitting said two other polarization modes in the lead-out fiber into two linearly, orthogonally polarized output beams and introducing a relative retardation between said output beams, the relative retardation being equal to the initial delay caused by said natural birefringence of the sensing fiber;

at least one step delay crystalline plate combined with said crystalline delay plate, said at least one step delay crystalline plate having polarization axes aligned in parallel to said polarization axes of the crystalline delay plate to extend said range of relative delays;

a Wollaston prism having polarization axes aligned in parallel with said polarization axes of said crystalline delay plate, for diverging said output light beams into slightly different directions thereon and introducing another range of relative delays increasing linearly from a beginning to an end of said Wollaston prism in a direction of diverging;

a recombiner for combining said orthogonally polarized output beams to produce an interference pattern;

a charged coupled device camera for detecting intensities across said interference pattern and determining position of a center of said interference pattern; and a computer having a software for tracking the position of the center of the interference pattern and determining said ambient parameter form said position 9. A method for measuring an ambient physical parameter, comprising the steps of:

a) emitting a low coherence, linearly polarized light beam in a predetermined polarization plane;

a') directing said light beam into a highly birefringent lead-in fiber having a polarization axis parallel to said polarization plane, said lead-in fiber propagating a polarization mode excited by said lightbeam;

b) connecting a highly birefringent sensing fiber to said lead-in fiber, said sensing fiber having two polarization axes rotated by an angle of 45° with respect to said polarization axis of the lead-in fiber to divide substantially equally said polarization mode propagating in the lead-in fiber into two polarization modes propagating with different velocities in said sensing fiber;

b') subjecting said sensing fiber to the ambient physical parameter so that a total relative delay between said two polarization modes in the sensing fiber is a sum of an initial delay caused by a natural birefringence of said sensing fiber and an additional delay induced by the isotropic ambient physical parameter when said sensing fiber is subjected thereto;

b") connecting a highly birefringent lead-out fiber to said sensing fiber, said lead-out fiber having two polarization axes rotated by an angle of 45° with respect to said polarization axes of the sensing fiber to divide substantially equally said two polarization modes propagating in the sensing fiber into two other polarization modes propagating in said lead-out fiber and subjecting said two other polarization modes to a relative delay substantially different from said total relative delay produced by said sensing fiber;

c) collecting an output light beam comprising said two other polarization modes from said lead-out fiber;

d) dividing said two other polarization modes into two linearly, orthogonally polarized output beams and subjecting said orthogonally polarized output beams to a range of relative delays covering said total relative delay produced by said sensing fiber;

e) recombining said orthogonally polarized output beams to produce an interference pattern;

f) detecting intensities across said interference pattern and determining a position of a center of said interference pattern; and g) determining said ambient parameter from the position of said center of said interference pattern.

10. A method according to claim 9, wherein said range of relative delays in step (d) is achieved by passing said output light beam comprising said two other polarization modes from said lead-out fiber through;

a crystalline delay plate having polarization axes aligned at an angle of 45° with respect to said polarization axes of the lead-out fiber, for splitting said two other polarization modes in the lead-out fiber into said two linearly, orthogonally polarized output beams and introducing a relative retardation between said output beams, the relative retardation being equal to the initial delay caused by said natural birefringence of the sensing fiber;

at least one step delay crystalline plate combined with said crystalline delay plate, said at least one step delay crystalline plate having polarization axes aligned in parallel to said polarization axes of the crystalline delay plate to extend said range of relative delays; and a Wollaston prism having polarization axes aligned in parallel with said polarization axes of said crystalline delay plate, for diverging said output light beams into slightly different directions thereon and introducing another range of relative delays increasing linearly from a beginning to an end of said Wollaston prism in a direction of diverging.

11. A method according to claim 10, wherein said isotropic ambient physical parameter is a hydrostatic pressure.

12. A method according to claim 10, wherein before said step (d), said output light beam comprising said two other polarization modes from said lead-out fiber is collimated, and wherein said step (f) comprises detecting said intensities at a plurality of points along a scanning line parallel to said direction of diverging, at a given distance from said prism.

13. A method according to claim 9, wherein said light beam has a coherence length of about 10–50 microns.

* * * * *